(12) United States Patent
Kapikian et al.

(10) Patent No.: US 7,932,074 B1
(45) Date of Patent: Apr. 26, 2011

(54) MULTIVALENT HUMAN-BOVINE ROTAVIRUS VACCINE

(75) Inventors: Albert Z. Kapikian, Rockville, MD (US); Robert M. Chanock, Bethesda, MD (US); Yasutaka Hoshino, Wheaton, MD (US)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 0 days.

(21) Appl. No.: 09/743,338

(22) PCT Filed: Jul. 27, 1999

(86) PCT No.: PCT/US99/17036
§ 371 (c)(1),
(2), (4) Date: Jan. 4, 2001

(87) PCT Pub. No.: WO00/06196
PCT Pub. Date: Feb. 10, 2000

Related U.S. Application Data

(60) Provisional application No. 60/094,425, filed on Jul. 28, 1998.

(51) Int. Cl.
*C12N 7/00* (2006.01)
*A61K 39/15* (2006.01)
(52) U.S. Cl. ................ 435/235.1; 424/205.1; 424/215.1
(58) Field of Classification Search ............... 424/199.1, 424/205.1, 93.1, 93.2, 93.6, 215.1; 435/235.1, 435/234
See application file for complete search history.

(56) References Cited

U.S. PATENT DOCUMENTS

| | | | |
|---|---|---|---|
| 4,571,385 A | | 2/1986 | Greenberg et al. |
| 6,113,910 A | * | 9/2000 | Clark et al. ................ 424/205.1 |

OTHER PUBLICATIONS

Bernstein et al. Lancet. 1999; 354: 287-290.*
Wandstradt et al. Ann Pharmacother. 1999 ; 33 (7-8): 833-9, abstract only.*
Brussow et al. Journal of General Virology. 1990; 71 (Pt 11): 2625-30, abstract only.*
Hoshino et al. Journal of Medical Virology, Apr. 1997: 51: 319-325.*
Midthun et al. Journal of Virology 1985, 53 (3): 949-954*
Midthun et al. Journal of Clinical Microbiology. 1986. 24 (5): 822-826.*
Gouvea et al., Identification of bovine and porcine rotavirus G types by PCR, Journal of Clinical Microbiology, 1994, 32(5): 1338-1340.*
Clark et al., Immune protection of infants against rotavirus gastroenteritis by a serotype 1 reassortant of bovine rotavirus WC3, J. Infect. Dis., 1990, 161(6):1099-104.*

Woode et al., "The Isolation of a Reovirus-Like Agent Associated with Diarrhoea in Colostrum-Deprived Calves in Great Britain," *Research in Veterinary Science* 16:102-105 (1974).
Bridger and Woode, "Neonatal Calf Diarrhoea: Identification of a Reovirus-Like (Rotavirus) Agent in Faeces by Immunofluorescence and Immune Electron Microscopy," *The British Veterinary Journal* 131:528-535 (1975).
Banatvala et al., "Rotaviral Infections in Human Neonates," *The Journal of the American Veterinary Association* 173:527-530 (1978).
Wyatt et al., "Reovirus-like Agents (Rotaviruses) Associated with Diarrheal Illness in Animals and Man." *Perspectives in Virology* 10:121-145 (1978).
Wyatt et al., "Human Rotavirus Type 2: Cultivation in vitro," *Science* 207:189-191 (1980).
Vesikari et al., "Immunogenicity and Safety of Live Oral Attenuated Bovine Rotavirus Vaccine Strain RIT 4237 in Adults and Young Children," *Lancet* 2:807-811 (1983).
Hoshino et al., "Serotypic Characterization of Rotaviruses Derived from Asymptomatic Human Neonatal Infections," *Journal of Clinical Microbiology* 21:425-430 (1985).
Kapikian et al., "Rhesus Rotavirus: A Candidate Vaccine for Prevention of Human Rotavirus Disease," Vaccines 85, Lerner et al., eds., Cold Spring Harbor Laboratory Press, Cold Spring Harbor, New York, pp. 357-367 (1985).
Midthun et al., "Reassortant Rotaviruses as Potential Live Rotavirus Vaccine Candidates," *Journal of Virology* 53:949-954 (1985).
Vesikari et al., "Dose-Response Study of RIT 4237 Oral Rotavirus Vaccine in Breast-Fed and Formula-Fed Infants," *Pediatric Infectious Diseases* 4:622-625 (1985).
Clark et al., "Immune Response of Infants and Children to Low-Passage Bovine Rotavirus (Strain WC3)," *The American Journal of Diseases of Children* 140:350-356 (1986).
Midthun et al., "Single Gene Substitution Rotavirus Reassortants Containing the Major Neutralization Protein (VP7) of Human Rotavirus Serotype 4," *Journal of Clinical Microbiology* 24:822-826 (1986).
Vesikari et al., "A Comparative Trial of Rhesus Monkey (RRV-1) and Bovine (RIT 4237) Oral Rotavirus Vaccines in Young Children." *The Journal of Infectious Diseases* 153:832-839 (1986).
Halsey et al., "Human-Rhesus Reassortant Rotavirus Vaccines: Safety and Immunogenicity in Adults, Infants, and Children," *The Journal of Infectious Diseases* 158:1261-1267 (1988). Kapikian et al., "Development of a Rotavirus Vaccine by a "Jennerian" and a Modified "Jennerian" Approach," Vaccines 88, Chanock et al., eds., Cold Spring Harbor Laboratory Press, Cold Spring Harbor, New York. pp. 151-159 (1988).
Flores et al., "Reactions to and Antigenicity of Two Human-Rhesus Rotavirus Reassortant Vaccine Candidates of Serotypes 1 and 2 in Venezuelan Infants," *Journal of Clinical Microbiology* 27:512-518 (1989).
Midthun et al., "Comparison of Immunoglobulin A (IgA), IgG, and IgM Enzyme-linked Immunosorbent Assays. Plaque Reduction Neutralization Assay, and Complement Fixation in Detecting Seroresponses to Rotavirus Vaccine Candidates," *Journal of Clinical Microbiology* 27:2799-2804 (1989).

(Continued)

*Primary Examiner* — Stacy B Chen
*Assistant Examiner* — Nicole Kinsey White
(74) *Attorney, Agent, or Firm* — Kilpatrick, Townsend & Stockton LLP

(57) ABSTRACT

The present invention provides vaccine compositions for protection against human rotaviral disease without significant reactogenicity. Human×bovine reassortant rotavirus comprising each of the four clinically most important VP7 serotypes of human rotavirus are combined in a multivalent formulation which provides a high degree of infectivity and immunogenicity without producing a transient febrile condition. Methods for producing an immunogenic response without producing a transient febrile condition are also provided.

11 Claims, No Drawings

OTHER PUBLICATIONS

Bernstein et al., "Evaluation of WC3 Rotavirus Vaccine and Correlates of Protection in Healthy Infants," *The Journal of Infectious Diseases* 162:1055-1062 (1990).

Clark et al., "Immune Protection of Infants against Rotavirus Gastroenteritis by a Serotype 1 Reassortant of Bovine Rotavirus WC3," *The Journal of Infectious Diseases* 161:1099-1104 (1990).

Clark et al., "Serotype 1 Reassortant of Bovine Rotavirus WC3, Strain WI79-9, Induces a Polytypic Antibody Response in Infants," *Vaccine* 8:327-332 (1990).

Flores et al., "Comparison of Reactogenicity and Antigenicity of M37 Rotavirus Vaccine and Rhesus-Rotavirus-Based Quadrivalent Vaccine," *Lancet* 336:330-334 (1990).

Green et al., "Homotypic and Heterotypic Epitope-Specific Antibody Responses in Adult and Infant Rotavirus Vaccines: Implications for Vaccine Development," *The Journal of Infectious Diseases* 161:667-679 (1990).

Nakagomi et al., "Isolation and Molecular Characterization of a Serotype 9 Human Rotavirus Strain," *Microbiology and Immunology* 34:77-82 (1990).

Perez-Schael et al., "Clinical Studies of a Quadrivalent Rotavirus Vaccine in Venezuelan Infants," *Journal of Clinical Microbiology* 28:553-558 (1990).

Taniguchi et al., "Antibody Response to Serotype-Specific and Cross-Reactive Neutralization Epitopes on VP4 and VP7 after Rotavirus Infection or Vaccination," *Journal of Clinical Microbiology* 29:483-487 (1991).

Kapikian et al. "An Update on the "Jennerian" and Modified "Jennerian" Approach to Vaccination of Infants and Young Children against Rotavirus Diarrhea," *Advances in Experimental Medicine and Biology* 327:59-69 (1992).

Madore et al., "Field Trial of Rhesus Rotavirus or Human-Rhesus Rotavirus Reassortant Vaccine of VP7 Serotype 3 or 1 Specificity in Infants," *The Journal of Infectious Diseases* 166:235-243 (1992).

Christy et al., "Evaluation of a Bovine-Human Rotavirus Reassortant Vaccine in Infants," *The Journal of Infectious Diseases* 168:1598-1599 (1993).

Flores et al., "Reactogenicity and Immunogenicity of a High-Titer Rhesus Rotavirus-Based Quadrivalent Rotavirus Vaccine," *Journal of Clinical Microbiology* 31:2439-2445 (1993).

Vesikari, "Clinical Trials of Live Oral Rotavirus Vaccines: the Finnish Experience," *Vaccine* 11:255-261 (1993).

Simasathien et al., "Vaccination of Thai Infants with Rhesus-Human Reassortant Tetravalent Oral Rotavirus Vaccine," *The Pediatric Infectious Disease Journal* 13:590-596 (1994).

Vesikari, "Bovine Rotavirus-Based Rotavirus Vaccines in Humans," *Viral Infections of the Gastrointestinal Tract*, Kapikian, ed., Marcel Dekker, Inc., New York pp. 419-442 (1994).

Kapikian, "Rhesus Rotavirus-Based Human Rotavirus Vaccines and Observations on Selected Non-Jennerian Approaches to Rotavirus Vaccination," *Viral Infections of the Gastrointestinal Tract*, Kapikian, ed., Marcel Dekker, Inc., New York pp. 443-470 (1994).

Bernstein et al., "Evaluation of Rhesus Rotavirus Monovalent and Tetravalent Reassortant Vaccines in US Children," *Journal of the American Medical Association* 273:1191-1196 (1995).

Treanor et al., "Evaluation of the Protective Efficacy of a Serotype 1 Bovine-Human Rotavirus Reassortant Vaccine in Infants," *The Pediatric Infectious Disease Journal* 14:301-307 (1995).

Clark et al., "The Development of Multivalent Bovine Rotavirus (Strain WC3) Reassortant Vaccine for Infants," *The Journal of Infectious Diseases* 174 (suppl.) 1:S73-80 (1996).

Clark et al., "WC3 Reassortant Vaccines in Children," *Archives of Virology* (suppl.) 12:187-198 (1996).

Kapikian et al., "Efficacy of a Quadrivalent Rhesus Rotavirus-Based Human Rotavirus Vaccine Aimed at Preventing Severe Rotavirus Diarrhea in Infants and Young Children," *The Journal of Infectious Diseases* 174 (Suppl. 1): S65-72 (1996).

Midthun et al., "Rotavirus Vaccines: an Overview," *Clinical . Microbiology Reviews* 9:423-434 (1996).

Rennels et al., "Safety and Efficacy of High-Dose Rhesus-Human Reassortant Rotavirus Vaccines-Report of the National Multicenter Trial," *Pediatrics* 97:7-13 (1996).

Vesikari et al., "Trials of Oral Bovine and Rhesus Rotavirus Vaccines in Finland: a Historical Account and Present Status," *Archives of Virology* ( suppl.) 12:177-186 ( 1996).

Hoshino et al., "Construction of Four Double Gene Substitution Human x Bovine Rotavirus Reassortant Vaccine Candidates: Each Bears Two Outer Capsid Human Rotavirus Genes, One Encoding P Serotype 1A and the Other Encoding G Serotype 1, 2, 3, or 4 Specificity," *Journal of Medical Virology* 51:319-325 (1997).

Joensuu et al., "Randomized Placebo-Controlled Trial of Rhesus-Human Reassortant Rotavirus Vaccine for Prevention of Severe Rotavirus Gastroenteritis," *Lancet* 350:1205-1209 (1997).

Timenetsky et al., "A Novel Human Rotavirus Serotype with Dual G5-G11 Specificity," *Journal of General Virology* 78:1373-1378 (1997).

Clements-Mann et al., "Safety and Immunogenicity of Live Attenuated Human-Bovine (UK) Reassortant Rotavirus Vaccines with VP7-specificity for Serotypes 1, 2, 3 or 4 in Adults, Children and Infants," *Vaccine* 17:2715-2725 (1999).

* cited by examiner

MULTIVALENT HUMAN-BOVINE ROTAVIRUS VACCINE

RELATED APPLICATIONS

The present application is a national stage application under 35 U.S.C. §371 of International Application No. PCT US99/17036, filed Jul. 27, 1999, which claims the benefit of U.S. Patent Application Ser. No. 60/094,425, filed Jul. 28, 1998.

BACKGROUND OF THE INVENTION

Rotaviruses are a major cause of acute dehydrating diarrhea in infants and young children. Rotavirus disease accounts for 25% to 30% of gastroenteritis deaths in infants and young children in developing countries and approximately 50,000-100,000 hospitalizations of children younger than five years of age in the United States. For this reason, a safe effective vaccine is needed to prevent severe rotavirus disease in infants and young children.

A primary strategy for rotavirus vaccine development has been based on a "Jennerian" approach, which takes advantage of the antigenic relatedness of human and animal rotaviruses and the diminished virulence of animal rotavirus strains in humans. Kapikian et al., in Vaccines 88, Chanock et al., eds., Cold Spring Harbor Laboratory Press, Cold Spring Harbor, N.Y., pp. 151-159 (1988). Several candidate live oral rotavirus vaccines have been developed using this approach, where an antigenically-related live virus derived from a nonhuman host is used as a vaccine for immunization against its human virus counterpart. Examples of animal rotaviruses that have been used to vaccinate humans include bovine rotavirus strain NCDV (RIT4237, Vesikari et al, Lancet, 2:807-811 (1983)), bovine rotavirus strain WC3 (Clark et al., Am. J. Dis. Child., 140:350-356 (1986)) and rhesus monkey rotavirus (RRV) strain MMU 18006 (U.S. Pat. No. 4,571,385, Kapikian et al., Vaccines 85, eds., Lerner et al., Cold Spring Harbor Laboratory Press, Cold Spring Harbor, N.Y., pp. 357-367 (1985)).

The protective efficacy among different monovalent bovine and monovalent simian rotavirus vaccines has proved to be variable (Vesikari in Viral Infections of the Gastrointestinal Tract (Kapikian, Ed., Marel Dekker, Inc. pp. 419-442 (1994): Kapikian ibid. pp. 443-470 (1994). Also, high concentrations of bovine rotavirus have been required to produce a satisfactory immune response in humans ($10^7$-$10^8$ plaque forming units (pfu)) (Vesikari et al., Ped. Inf. Dis. 4:622-625 (1985), Bernstein et al. J. Infect. Dis. 162:1055-1062 (1990)). The variable efficacy of these compositions can in part be attributed to the fact that the target population of two- to five-month old infants characteristically developed a homotypic immune response following vaccination (Kapikian et al., Adv. Exp. Med. Biol., 327:59-69 (1992); Bernstein et al., J. Infect. Dis. 162:1055-1062 (1990); Green et al. J. Infect. Dis. 161:667-679 (1990); and Vesikari, Vaccine. 11:255-261 (1993)).

Clinically relevant human rotaviruses are members of the Group A rotaviruses. These viruses share a common group antigen mediated by VP6, a protein located on the virus intermediate shell. Also, serotype specificity depends on the presence of the VP4 (protease sensitive or P type) and VP7 (glycoprotein or G type) proteins located on the virus outer shell (also often referred to as the virus capsid), both of which independently induce neutralizing antibodies. Kapikian et al. In Virology, Fields, ed. pps. 1353-1404 (1995).

Group A rotaviruses that infect humans have been classified into ten distinct VP7 serotypes by neutralization assays. Amino acid sequence analysis has indicated that within each serotype amino acid identity within two major variable regions was high (85-100%); however, amino acid identity between strains of different serotypes was significantly less (Green et al., Virol. 168:429-433 (1989); Green et al., Virol. 161:153-159 (1987); and Green et al., J. Virol. 62:1819-1823 (1988)). Concordance between relationships among rotaviruses as determined by virus neutralization assay or sequence analysis of VP7 has been demonstrated. Therefore, a reference strain can be routinely used in clinical studies as a representative of rotavirus strains within its serotype.

To achieve protection against each of the four epidemiologically and clinically important G serotypes (VP7) (numbered 1, 2, 3, and 4), the Jennerian approach has been modified by the production of reassortant rotaviruses. Reassortant rotavirus strains were constructed by coinfecting tissue culture cells with a rotavirus of animal origin (i.e., rhesus or bovine rotavirus) and a human rotavirus strain. Reassortant viruses produced during coinfection that contained a single human rotavirus gene encoding VP7 from the human strain and the 10 remaining rotavirus genes from the animal strain were selected by exposing the progeny of the coinfection to a set of monoclonal antibodies directed to the VP7 of the animal strain. (See, for example. U.S. Pat. No. 4,571,385; Midthun et al. J. Clin. Microbiol. 24:822-826 (1986); and Midthun et al. J. Virol. 53:949-954 (1985)).

Studies of human×rhesus rotavirus reassortants and human×bovine reassortants containing the VP7 gene from a human strain have demonstrated that the VP4 neutralization protein of the animal rotavirus parent dominates the immune response in infants vaccinated with these human×animal rotavirus reassortants. This probably reflects the absence of animal rotavirus VP4 antibodies among the antibodies transferred from the mother to the infant in utero. Nevertheless, the immune response to human rotavirus VP7 that is partially blunted by maternally derived VP7 antibodies is sufficient to provide protection and thus VP7 antibodies form the basis of the modified Jennerian approach (Flores et al., J. Clin. Microbiol. 27:512-518 (1989); Perez-Schael et al., J. Clin. Microbiol. 28:553-558 (1990); Flores et al., J. Clin. Microbiol. 31:2439-2445 (1993); Christy et al., J. Infect. Dis. 168:1598-1599 (1993); Clark et al., Vaccine 8:327-332 (1990); Treanor et al., Pediatr. Infect. Dis. J. 14:301-307 (1995); Madore et al. J. Infect. Dis. 166:235-243 (1992); and Clark et al., J. Infect. Dis. 161:1099-1104 (1990).

In studies using a single rhesus rotavirus reassortant bearing a single human rotavirus gene, namely the gene that encodes VP7, it was observed that the protective immunological response of such a reassortant was characteristically homotypic in infants less than six months of age (Green et al., J. Inf. Dis. 161:667-679 (1990)). This observation provided further evidence for the importance of VP7-associated immunity in immunization against rotavirus disease.

The general experience with monovalent and quadrivalent human×rhesus rotavirus reassortant vaccines has been that a transient low-level febrile episode occurs in about one-third of young infants 3 to 4 days after vaccination. Bernstein et al., JAMA 273:1191-1196 (1995); Flores et al., Lancet 336:330-334 (1995); Perez-Schael et al., J. Clin. Microbiol. 28:553-558 (1990); Flores et al., J. Clin. Microbiol. 31:2439-2445 (1990); Halsey et al., J. Infect Dis. 158:1261-1267 (1988); Taniguichi et al., J. Clin. Microbiol. 29:483-487 (1991); Simasathien et al., Pediatr. Infect. Dis. J. 13:590-596 (1994); Madore et al., J. Infect. Dis. 166:235-243 (1992); and Joensuu et al., Lancet 350:1205-1209 (1997).

Results of studies in humans with bovine rotavirus strains NCDV and WC3 (VP7 serotype 6) indicate that these particular bovine rotavirus strains do not appear to cause fever or other reactions. It should be noted that serotype 6 VP7 is not known to be present on human rotaviruses that are important in human rotavirus disease. Also, a bovine rotavirus was not found to be as immunogenic as the rhesus rotavirus when administered to humans. The bovine rotavirus strain NCDV (RIT4237 vaccine) has been evaluated in more than five efficacy trials in infants and young children. In these trials, the bovine RIT4237 vaccine was administered at a dose range of $10^{7.8}$ to $10^{8.3}$ tissue culture infectious doses $_{50}$ ($TCID_{50}$), with the usual dosage exceeding $10^{8.0}$ $TCID_{50}$. Also, in a dose-response study, Vesikari et al., *Ped. Infect. Dis.*, 4:622-625 (1985)) observed that 15% (2/13) of four- to six-month old infants developed a homotypic antibody response when the vaccine was administered at a dose of $10^{6.3}$ $TCID_{50}$; 71% (10/14) when administered at a dose of $10^{7.2}$ $TCID_{50}$, and 100% when administered at a dose of $10^{8.3}$ $TCID_{50}$. Thus, the dose for this bovine rotavirus strain that produced an optimal immunogenicity was determined to be in the range of $10^{8.0}$ $TCID_{50}$.

In a direct comparison of the infectivity and immunogenicity of rhesus rotavirus and bovine rotavirus in humans, $10^5$ plaque forming units (pfu) of rhesus rotavirus (RRV vaccine) or $10^{8.3}$ pfu of RIT4237 was administered to children six to eight months of age. (Vesikari et al., *J. Infect. Dis.* 153:832-839 (1986)). The RRV vaccine induced a homotypic neutralizing antibody response in 81% of vaccinees, whereas the two thousand fold greater dose of the bovine RIT4237 vaccine induced homotypic neutralizing antibodies in only 45% of vaccinees, which was a statistically significant difference.

Efficacy trials were also conducted with the WC3 bovine rotavirus strain. In these trials, the WC3 strain was administered to infants and young children at a dose range of $10^{7.0}$ to $10^{7.3}$ pfu. (Clark et al., *Am. J. Dis. Child.* 140:350-356 (1986)). Although data regarding the dose required for significant immunogenicity was not provided, Clark et al. noted that the WC3 strain appears to possess safety characteristics similar to those of RIT4237, yet was immunogenic at a dose at least five fold less than that used with bovine RIT4237, though this immunogenicity still required a dose that was considerably greater than that of rhesus rotavirus vaccine.

The WC3 rotavirus strain has been used as one of the parent strains for generating reassortants with various human rotavirus strains. (Clark et al., *J. Infect. Dis.* (suppl.) 174:73-80 (1996)). In one efficacy trial, $10^{7.3}$ pfu of a monovalent reassortant of WC3 and a human rotavirus VP7 serotype 1 was administered on a three dose schedule to infants and young children. (Treanor et al., *Ped. Inf. Dis. J.* 14:301-307 (1995)). Immunogenicity data was not reported for this trial. In another efficacy study, a quadrivalent formulation was used which contained three human VP7 reassortants of bovine rotavirus WC3 with a human rotavirus VP7 serotype of 1, 2, or 3 and as a fourth component, a human x bovine reassortant bearing a human rotavirus VP4 protein with the remaining genes derived from the bovine rotavirus WC3. Each of the three VP7 reassortants was used at a dose of $10^{7.0}$ pfu, while the VP4 reassortant was administered at a dosage of $5\times10^{6.0}$ pfu. (Clark et al., *Arch. Virol.* (suppl.) 12:187-198 (1996); Clark et al. *J. Infect. Dis.* (suppl.) 174:73-80 (1996); Vesikari et al. *Arch. Virol.* (suppl.) 12:177-186 (1996)). Immunogenicity data for this trial also was not reported, but these studies indicate that to characteristically produce a protective response similar to that obtained with the rhesus rotavirus or human×rhesus reassortant vaccines a dosage of $10^7$ to $10^{8.3}$ pfu was required. (Clark et al. *Arch. Virol.* (suppl.) 12:187-198 (1996); Vesikari et al. *Arch. Virol.* (suppl.) 12:177-186 (1996)). This dosage is 10 to 100 times higher than that for the rhesus rotavirus and human×rhesus rotavirus reassortant vaccine compositions.

Multivalent rotavirus vaccine compositions have been developed. In particular, three human×rhesus rotavirus reassortants representing human serotypes 1, 2 and 4 have been combined with a rhesus rotavirus strain (RRV) (the latter sharing neutralization specificity with human serotype 3) to form a quadrivalent vaccine composition (Perez-Schael et al., *J. Clin. Microbiol.* 28:553-558 (1990), Flores et al., *J. Clin. Microbiol.* 31:2439-2445 (1993)). As with the monovalent rhesus rotavirus, the human×rhesus reassortant rotavirus vaccine compositions were found to produce a transient low level febrile condition in approximately 15% to 33% of the infants vaccinated (Perez-Schael et al. supra). This transient febrile episode or condition, although generally considered acceptable by the parents and health care providers of the clinical trial, could possibly be a deterrent in certain situations, such as, in premature infants who may have low levels of passively acquired maternal antibodies to rotavirus and the like.

Although the animal rotavirus-based rotavirus vaccine composition presently licensed by the United States Food and Drug Administration provides an important level of protection in humans against rotavirus infection, a multivalent vaccine composition with both high infectivity and which produce little or no febrile response is desirable, especially for certain clinical situations. Surprisingly, the present invention fulfills these and other related needs.

SUMMARY OF THE INVENTION

The present invention provides an immunogenic composition of human×bovine reassortant rotaviruses. The human× bovine reassortants are provided in multivalent compositions in an amount sufficient to induce an immune response to each serotype of human rotavirus of current and future clinical importance in a dose of sufficient infectivity to overcome previous practical limitations of the art without causing a transient low level fever in a human host. Further components of the immunogenic composition can include a physiologically acceptable carrier and optionally an adjuvant to enhance the immune response of the host. In certain embodiments, the human×bovine reassortant rotavirus VP7 antigen is derived from a human parent rotavirus strain. e.g., from a human rotavirus of serotype 1, serotype 2, serotype 3, serotype 4, serotype 5, serotype 9, or from a bovine parent rotavirus strain of serotype 10. The remaining genes which encode the other rotavirus proteins are derived from a bovine rotavirus strain. In a preferred embodiment the bovine rotavirus UK-Compton strain is used. A particularly preferred immunogenic composition which provides coverage for VP7 serotypes 1, 2, 3 and 4 comprise a quadrivalent composition which includes human×bovine rotavirus reassortants D×UK, DS-1×UK, P×UK and ST3×UK, respectively.

In further embodiments, additional human×bovine rotavirus reassortants corresponding to human rotavirus VP7 serotypes 5, and/or 9, or a bovine×bovine reassortant crossreactive with human rotavirus VP7 serotype 10, or a human× bovine reassortant rotavirus containing a human rotavirus VP4 serotype 1A can be included to provide an immunogenic composition with a broader range of use. Of particular interest are a pentavalent composition comprising rotavirus reassortants D×UK, DS-1×UK, P×UK, ST-3×UK and Wa(VP4)× UK stains; a hexavalent composition comprising the pentavalent composition noted above, plus a VP7, serotype 9×UK strain, and a septavalent composition comprising the hexavalent composition noted above plus a VP7 serotype 5×UK strain or the septavalent composition noted above plus a VP7 serotype 10×UK strain. Additional strains of rotavirus as they are recognized to produce significant disease in humans can also be made into bovine rotavirus reassortants and added to an immunogenic composition of the present invention. The immunogenic composition of the present invention will typically be formulated in a dose of less than about $10^{6.0}$ plaque forming units of each rotavirus VP7 or VP4 serotype reassortant. It is particularly preferred that the dosage is between about $10^5$ to less than about $10^6$ plaque forming units.

In other embodiments, the invention provides methods for stimulating the immune system to produce an immunogenic response to human rotavirus antigens with little or no accompanying transient low level fever. These methods comprise administering to an individual an immunogenically sufficient amount of a multivalent human×bovine reassortant rotavirus composition comprising at least four VP7 serotypes of human rotavirus. In a preferred embodiment the human×bovine reassortant rotavirus which comprise the composition include a human rotavirus serotype 1× bovine rotavirus strain UK, a human rotavirus serotype 2× bovine rotavirus strain UK, a human rotavirus serotype 3× bovine rotavirus strain UK, and a human rotavirus serotype 4× bovine rotavirus strain UK. The multivalent composition can also include, but is not limited to, i.e., a human×bovine reassortant rotavirus of serotype 5, and/or serotype 9, or a bovine×bovine reassortant rotavirus with human rotavirus VP7 serotype 10 specificity, or a human rotavirus serotype VP4 1A×bovine rotavirus UK reassortant and the like. Further, as additional rotavirus serotypes are recognized as important in human disease, they too can be added to an immunogenic composition of the present invention and used in methods for stimulating the immune system to produce an immunogenic response to currently recognized and newly recognized rotaviruses of clinical significance.

DESCRIPTION OF THE SPECIFIC EMBODIMENTS

The present invention provides immunogenic rotavirus compositions for use in humans. The compositions described herein are produced by combining monovalent reassortant human×animal rotaviruses so as to provide one of each of the most clinically relevant serotypes of group A human rotavirus in a formulation which induces a rotavirus-specific antibody response without an attendant transient low level febrile response.

Thus, the immunogenic compositions of the invention specifically comprise a combination of reassortant human×bovine rotaviruses and a physiologically acceptable carrier to form a multivalent composition. In a particular embodiment, the multivalent immunogenic composition comprises a combination of four reassortant human×bovine rotaviruses of the clinically relevant serotypes of human rotavirus that are most prevalent world-wide, to form a quadrivalent composition. The immunogenic composition is administered in an immunogenically sufficient amount to an individual in need of immunological protection against rotavirus, such as, e.g. an infant, child or adult. The composition elicits the production of an immune response that is at least partially protective against symptoms of serious rotaviral disease, such as severe diarrhea and dehydration, when the individual is subsequently infected with a wild-type human rotavirus strain. As the reassorted viruses of the immunogenic composition infect the host alimentary tract, some mild disease may occur as a result of the vaccination, but typically the immunogenic composition of the present invention will not cause clinically relevant fever or reaction in the vaccinee. Following vaccination, there are detectable levels of host engendered serum antibodies which are capable of neutralizing the serotypes of rotavirus that make up the immunogenic composition. In particular, the multivalent immunogenic composition of the present invention will produce an immunological response to most, if not all, of the clinically relevant group A human rotaviruses prevalent in different settings. The teachings of the present invention are not limited to those human rotavirus serotypes currently recognized of clinically relevant, but also include those serotypes of human rotavirus that emerge as clinically relevant in the future.

The reassorted rotavirus which is a component of the multivalent immunogenic composition of the present invention is in an isolated and typically purified form. By isolated is meant to refer to reassorted rotavirus that has been separated from other cellular and viral products of its manufacture, such as wild type virus and other heterologous components of a cell culture or other systems.

Generally, rotavirus reassortants are produced by coinfection of mammalian cells in culture with a tissue culture-adapted animal rotavirus. i.e., bovine, rhesus, and the like, and a tissue culture-adapted human rotavirus. Typically. African green monkey kidney (AGMK) cells are used as the host cells for co-infection. Following co-infection with the animal and human rotavirus strains, selection of the desired reassortant is typically achieved by exposing the growth yield of co-infected cultures to neutralizing antibodies specific for the protein product of the animal rotavirus gene that is to be replaced by the human rotavirus gene (See, U.S. Pat. No. 4,571,385, incorporated herein by reference). In particular, polyclonal serum or monoclonal antibody specific for bovine rotavirus VP7 and/or VP4 proteins can be used. After several rounds of plaque purification and subculture, selected reassortants are characterized for serotype and genotype. Serotype is typically determined by plaque reduction neutralization (PRN) assay or enzyme immunoassay. Genotype is typically determined by gel electrophoresis and RNA-RNA hybridization of the viral genome. Rotavirus reassortants having only the human VP7 or VP4 gene are typically selected for the present multivalent immunogenic compositions. Reassortants comprising multiple human rotavirus genes can also be used. In this regard, reassortant rotaviruses of interest are particularly those encoding the human rotavirus VP7 and/or the human rotavirus VP4 gene products.

In the present invention, particularly preferred rotavirus reassortants are human rotavirus and bovine rotavirus reassortants comprising the human rotavirus gene encoding VP7 and the remaining ten rotavirus genes of bovine rotavirus origin. The bovine rotavirus strain UK (Woode et al., *Res. Vet. Sci.* 16:102-105 (1974); Bridger and Woode, *Br. Vet. J.*, 131: 528-535 (1975)) is particularly preferred because of its pedigree and as demonstrated by the present invention its higher level of infectivity in humans. The high infectivity level of the UK bovine rotavirus reassortants demonstrated herein means a lower dose is needed, and consequently the manufacturing cost per dose should be significantly less than other presently known bovine rotavirus reassortant vaccines. Other animal rotavirus strains can also be used to make reassortant rotavirus as long as the compositions are capable of inducing a serologic response in a vaccinee when administered at a dosage of less than $10^{6.0}$ plaque forming units for each rotavirus serotype and do not produce a transient low level febrile response. For example, in certain embodiments the reassortant rotavirus comprises an animal VP7 antigen which is immunologically cross-reactive with human VP7 serotype 10. This reassortant rotavirus can be a bovine×bovine reassortant.

In an alternative embodiment, reassortant rotavirus of a specific serotype can be produced using a previously obtained reassortant. For example, to produce additional bovine UK reassortants the human rotavirus VP7 serotype 1 D strain× bovine UK reassortant HD/BRV-1 (ATCC VR-2069) can be used to produce human rotavirus×bovine UK reassortants having human VP7 serotypes of 2, 3, 4, 9, and/or bovine rotavirus VP7 serotype 10. The methods used are similar to those described above except polyclonal or monoclonal neutralizing antibody specific for the VP7 serotype of the parental human rotavirus reassortant is used to select for new reassortants of the desired human (and/or bovine) rotavirus VP7 serotype. It is also contemplated as part of the present invention that as other clinically relevant human VP4 or VP7 serotypes are isolated and identified reassortant rotavirus of the newly discovered serotype can be produced by the described methods.

Propagation of the reassorted rotavirus can be in a number of cell cultures which support rotavirus growth. Preferred cell cultures for propagation of rotavirus reassortants for vaccine use include primary or secondary simian African green monkey kidney cells (AGMK), qualified diploid simian FRhL-2 cells and qualified simian heteroploid Vero cells. Cells are typically inoculated with rotavirus reassortants at a multiplicity of infection ranging from about 0.1 to 1.0 per cell, or more, and are cultivated under conditions appropriate for viral replication, for about 3-5 days, or as long as necessary for virus to reach an adequate titer. Rotavirus reassortants are harvested from infected cell culture and separated from cellular components, typically by well known clarification procedures, e.g., centrifugation, and may be purified as desired using procedures well known to those skilled in the art.

In a preferred embodiment for use as an immunogenic composition, a human x bovine reassortant rotavirus of serotype 1, serotype 2, serotype 3 and serotype 4 are used as a quadrivalent vaccine. Typically, the human×bovine reassortant rotavirus of each of the four serotypes will be admixed to form a combined composition for simultaneous administration. The final ratio of each rotavirus serotype is determined by the immunogenicity of the individual rotavirus reassortants. Although not preferred, each human×bovine reassortant, or a combination thereof, can also be administered in a sequential manner to provide an effective vaccine formulation.

In other preferred embodiments the human×bovine reassortant rotavirus of serotype 1, serotype 2, serotype 3 and serotype 4 are combined with a human×bovine reassortant rotavirus of VP7 serotype 5 and/or 9, a bovine×bovine reassortant rotavirus of VP7 serotype 10, and/or a human×bovine reassortant rotavirus of VP4 serotype 1A to yield a multivalent immunogenic composition. The additional reassortant rotaviruses just described can be used in any combination for use as a hexavalent, septavalent, or octavalent immunogenic composition.

Human×bovine reassortant rotavirus multivalent immunogenic compositions of the present invention contain as an active ingredient an immunogenically effective amount of each of at least the four clinically most important VP7 serotypes of human rotavirus as described herein. In particular, each antigenically distinct human rotavirus reassortant is administered at a dosage of less than $10^{6.0}$ plaque forming units. The immunogenic composition may be introduced into a host, particularly humans, with a physiologically acceptable carrier and/or adjuvant. Useful carriers include.e.g., citrate-bicarbonate buffer, buffered water, normal saline, and the like. The resulting aqueous solutions may be packaged for use as is, or lyophilized, as desired, using lyophilization protocols well known to the artisan. Lyophilized virus will typically be maintained at about 4° C. When ready for use the lyophilized preparation is combined with a sterile solution prior to administration, as mentioned above.

The compositions may contain pharmaceutically acceptable auxiliary substances as required to approximate physiological conditions, such as pH adjusting and buffering agents and the like, for example, sodium acetate, sodium lactate, sodium chloride, potassium chloride, calcium chloride, sorbitan monolaurate, tri-ethanolamine oleate, citrate-bicarbonate, or the like. When the composition is administered orally it may also be necessary to provide the individual a buffer solution to partially neutralize stomach acid and protect the reassortant rotavirus while passing to the intestine. Buffer solutions appropriate for this use include sodium bicarbonate, citrate bicarbonate, or the like. Upon immunization with a human×bovine reassortant rotavirus composition of the present invention, particularly via the oral route, the immune system of the host responds to the composition by producing both local secretory and serum antibodies specific for the rotavirus proteins. As a result of the administration of the composition, the host becomes at least partially or completely immune to human rotavirus disease caused by a wild-type strain that corresponds to the immunizing serotype(s). If wild-type virus infection does occur, the host is resistant to developing moderate or severe rotaviral disease, particularly of the gastrointestinal tract.

The multivalent immunogenic compositions of the present invention containing the human×bovine reassortant rotaviruses are administered to a person, particularly an infant, susceptible to or otherwise at risk of rotavirus disease to induce the individual's own immune response capabilities. Such an amount is defined to be an "immunogenically effective dose." Immunogenicity or "immunogenically effective dose" as used in the present invention means the development in a vaccinee of a cellular and/or antibody mediated immune response to the vaccine composition. Usually such a response consists of the vaccinee producing serum antibodies, B cells, helper T cells, suppressor T cells, and/or cytotoxic T cells directed specifically to an antigen or antigens included in the vaccine composition of the present invention. A four-fold or greater rise above a preinoculation antibody titer following immunization measured by a rotavirus group-specific, or rotavirus serotype-specific assay is considered a significant response.

In this use, the precise amount of each human×bovine reassortant rotaviral serotype in a particular immunogenic composition depends on the patient's age, state of health and weight, the mode of administration, the nature of the formulation, etc., but generally the range was from about $10^4$ to about $10^6$ plaque forming units, preferably from about $10^5$ to less than $10^6$ plaque forming units (pfu) of each serotype per patient.

In any event, the formulations for the immunogenic composition should provide a quantity of each human×bovine reassortant rotavirus of the invention sufficient to induce an individual's immune response against rotavirus disease. Preferably, this immune response will effectively protect the individual against serious or life-threatening rotavirus disease without being "reactogenic." As used herein, "reactogenic" or reactogenicity denote a mild transient fever occurring during the week following administration of the immunogenic composition. A fever is defined in the context of the present invention as the development of an oral temperature of greater than or equal to 38° C. in an adult, or a rectal temperature of greater than or equal to 38.1° C. in a pediatric vaccinee.

In some instances it may be advantageous to combine the preferred quadrivalent human×bovine reassortant rotaviral compositions of the present invention with other serotypes of human rotavirus or other infectious agents, particularly, other gastrointestinal viruses. For example, the quadrivalent human×bovine reassortant rotaviral compositions of the present invention can further include, for example, human× bovine reassortant rotavirus of serotype 5 (Timenetsky et al., *J. General Virol.* 78:1373-1378 (1997)), and/or serotype 9 (Nakagomi et al. *Microbiol. Immunol.* 34:77-82 (1990)), and/or bovine×bovine reassortant rotavirus which is cross reactive with human rotavirus serotype 10 and/or human×bovine reassortant rotavirus of VP4 serotype 1A. Administration can be simultaneous (but typically separately) or sequentially with another possible gastrointestinal virus vaccine, such as a human calicivirus (e.g., Norwalk virus) or related vaccine.

Single or multiple administrations of the immunogenic compositions of the invention can be carried out. In neonates and infants, multiple administrations may be required to elicit a sufficient level of immunity, particularly where there are high levels of maternally derived antibodies specific for rotavirus. Administration should begin within the first 2-4 months of life, and continue at intervals such as one to two months or more after the initial immunization, or as necessary to induce and maintain sufficient levels of immunity against human rotavirus infection. Similarly, adults who are particularly susceptible to repeated or serious rotavirus disease, such as, for example, health care workers, day care workers, family members of young children, the elderly, etc. may require multiple immunizations to establish and/or maintain an effective immune response. Levels of induced immunity can be monitored by measuring amounts of rotavirus group-specific antibodies or serotype-specific neutralizing antibodies in serum and secretions, and dosages adjusted or vaccinations repeated with one or more serotypes of a multivalent reassortant rotavirus composition of the present invention when necessary to maintain desired levels of immunity.

The following examples are offered by way of illustration, not by way of limitation.

Example I

This Example describes the production of rotavirus reassortants derived from human rotavirus strains D (VP7:1), DS-1 (VP7:2), P (VP7:3) and ST3 (VP7:4), and bovine UK Compton (UK) rotavirus and the evaluation of the safety, immunogenicity and reactogenicity of each reassortant individually in adults, children, and infants.

Human×bovine reassortant rotavirus strains representing VP7 serotypes 1, 2, 3 and 4 were derived from the bovine UK Compton (UK) strain and from human rotavirus strains D (VP7 serotype 1, ATCC VR-970), DS-1 (VP7 serotype 2; Wyatt et al., *Perspect. Virol.* 10:121-145 (1978)) and P (VP7 serotype 3; Wyatt et al., *Science* 207:189-171 (1980)), and ST3 (VP7 serotype 4; Banatvala et al., *J. Am. Vet. Med. Assoc.* 173:527-530 (1978)). Human rotavirus strains D, DS-1, and P were recovered from stools of children hospitalized with diarrhea; Strains D and DS-1 were propagated and passaged in gnotobiotic calves (Wyatt et al., 1978, supra; and Midthun et al., 1985, *J. Virol.* 53:949-954) and later grown only in tissue culture, while strain P was grown only in AGMK tissue culture. Human rotavirus strain ST3 was isolated from a stool of an asymptomatic neonate and passaged in AGMK cells. The bovine UK Compton rotavirus strain was isolated in primary calf kidney cells from the stool of a colostrum-deprived calf with diarrhea. (Woode et al., *Res. Vet. Sci.* 16:102-105 (1974)). The further passage of this virus in primary calf kidney cells was carried out by Flewett et al., at the Regional Virus Laboratory, East Birmingham Hospital, Birmingham, England and sent to the National Institutes of Health, Bethesda, Md. At the NIH the virus was serially passaged in primary bovine embryonic kidney cells, primary AGMK cells, and in diploid simian DBS-FRhL cells. The seed pool contained virus that was plaque purified in AGMK cells and passaged in primary calf kidney cell culture.

The individual human×bovine rotavirus reassortants with a single VP7 encoding gene derived from human rotavirus D, DS-1, P or ST3 strain and the remaining 10 genes derived from the bovine UK strain (lot BR-3, clone 22) have been described (Midthun et al. *J. Clin. Microbiol.* 24:822-826 (1986) and Midthun et al., *J. Virol.* 53:949-954 (1985), U.S. Pat. No. 4,571,385 all of which are incorporated herein by reference). The D×UK, DS-1×UK. P×UK and ST3×UK vaccine suspensions used in these clinical trials. i.e., lot HD BRV-1, clone 47-1-1 (ATCC VR-2069 and ATCC VR-2617), $10^{5.8}$ pfu/ml; lot HDS1 BRV-1, clone 66-1-1 (ATCC VR-2616), $10^{5.3}$ pfu/ml; lot HP BRV-2, clone 22-1-1 (ATCC VR-2611), $10^{5.3}$; and lot ST3 BRV-2, clone 52-1-1 (ATCC VR-2612), $10^{5.8}$ pfu/ml respectively, were prepared and successfully safety tested to confirm freedom from adventitious agents in accordance with the guidelines of the U.S. Food and Drug Administration as well known to the skilled artisan.

All pediatric studies and one study in adults with the D×UK human×bovine reassortant rotavirus were conducted in a randomized, placebo-controlled manner to assess the safety and immunogenicity of each candidate rotavirus vaccine strain. The safety of each human×bovine reassortant rotavirus was evaluated sequentially in adults 18 to 45 years of age, in children 6 to 60 months of age, and finally in infants 1.5 to 5.9 months of age. The various studies were carried out at either the Johns Hopkins University Center for Immunization Research, Baltimore, Md. or the Vaccine Clinic, Vanderbilt University, Nashville, Tenn.

The criteria for selection of adult and pediatric subjects for rotavirus vaccine trials have been described in Halsey et al., *J. Infect. Dis.* 158:1261-1267 (1988). An undiluted dose of each rotavirus reassortant was evaluated in adults initially. Subsequently, a 1:10 dilution of each reassortant and later an undiluted dose ($10^{5.3}$ pfu) of P×UK were evaluated in children 6 to 60 months of age. After the safety of each reassortant had been demonstrated in these children, a 1:10 dose and an undiluted dose of D×UK and DS-1×UK were also evaluated sequentially in infants <6 months old. Since it appeared that an undiluted dose of these reassortants was required to infect the majority of the young infants, the P×UK or ST3×UK reassortant was administered undiluted to infants <6 months old.

Initially, the safety of $10^{5.8}$ pfu of the D×UK reassortant rotavirus strain was evaluated in five healthy adult volunteers who had a low level of VP7 serotype 1 specific neutralizing antibodies in their serum. The clinical procedures for the studies with adults were those previously described in Halsey et al., supra, with a few exceptions. Briefly, all subjects fasted for at least 1 hour before and after each feeding of rotavirus. Each adult volunteer drank 120 ml of distilled water with 2 g of $NaHCO_3$, followed 1 min. later by 1 ml of undiluted candidate vaccine suspended in 30 ml of buffered solution or 31 ml of placebo (buffered solution without the vaccine). Oral temperature was recorded twice daily and any elevated temperature was rechecked within 20 minutes. Stool samples were collected for 7 days following the administration of rotavirus and the consistency and number of stools recorded and any symptoms were also recorded daily for 7 days after vaccination.

Most of the clinical procedures for the pediatric studies were also identical to those described by Halsey (supra.), with a few exceptions. Briefly, routine childhood immunizations appropriate for the child's age were given on schedule, and at least two weeks before or after administration of rotavirus or placebo. After fasting one hour, each pediatric subject was randomized to receive rotavirus or placebo in a 2:1 ratio. Each child drank 30 ml of infant formula (Similac; Ross Laboratories, Columbus, Ohio) mixed with 0.4 g of $NaHCO_3$, and then drank 1 ml of rotavirus reassortant or placebo (buffered formula or Eagle's Minimal Essential Medium). Infants <6 months of age who received the $10^{5.8}$ pfu of D×UK rotavirus reassortant were offered a second dose of this virus 4 to 12 weeks after the first dose in an attempt to increase immunogenicity.

In studies of the D×UK and DS-1×UK reassortants, rectal temperatures were taken once or twice a day, and symptoms, if any, were recorded daily. Parents were instructed to collect a stool sample daily and record the number and consistency of stools passed by their child daily. Procedures for pediatric studies of P×UK and ST-3×UK were similar with slight modifications.

Study subjects were considered to have "rotavirus-like illness." (i.e., an illness that could possibly be caused by a rotavirus, if they had diarrhea, or any episode of frank vomiting or fever during the 7-day period after oral administration of rotavirus. Diarrhea was defined as three or more unformed stools within 48 hours. Fever was defined as an oral temperature $\geq 37.8°$ C. in adults or a rectal temperature $\geq 38.1°$ C. in pediatric subjects, confirmed within 10-20 minutes.

Blood was collected from each study participant before and 4-6 weeks after administration of rotavirus for measurement of rotavirus-specific antibodies and serum alanine aminotransferase (ALT) level: the latter was used to ascertain whether the vaccine adversely affected liver functions. In adults, an additional blood specimen was also collected one week after administration of rotavirus and used for measurement of ALT level.

Prevaccination and postvaccination sera were tested for rotavirus-specific IgA and IgG antibodies by ELISA, using rhesus rotavirus as a group-specific antigen as described in Midthun et al., *J. Clin. Microbiol.* 27:2799-2804 (1989) and Hoshino et al., *J. Clin. Microbiol.* 21:425-430 (1985); each incorporated by reference herein. Paired sera were also tested by plaque reduction neutralization (PRN) antibody assay as described in Midthun et al., *J. Clin. Microbiol.* 27:2799-2804 (1989). Rotaviruses used in the PRN assay included: Wa (serotype 1), DS-1 (serotype 2), P (serotype 3) and ST3 or VA70 (serotype 4) human rotavirus strains plus: D×UK, DS-1×UK, P×UK, and ST3×UK reassortant strains and the UK (Compton) bovine rotavirus strain. A fourfold or greater rise in antibody titer in the postvaccination serum compared to the prevaccination serum measured by ELISA IgA or ELISA IgG, or PRN antibody assay was considered a significant response.

Frozen stool samples were thawed and made into 10% stool suspensions in veal infusion broth. The stool suspensions were inoculated onto simian MA104 cell culture tubes and incubated in a roller drum at 37° C. for 7 days. The supernatant from the cell culture was blind passaged onto fresh simian MA104 cell culture tubes and incubated at 37° C. for 7 days. The 10% stool suspension and the supernatants from each set of cultures were stored at −20° C., until later when they were thawed and tested for rotavirus by ELISA. Selected rotavirus positive stool specimens collected following vaccination were serotyped by polymerase chain reaction to determine the serotype of rotavirus shed (Gouvea et al., *J. Clin. Microbiol.* 28:276-282 (1990) and Gouvea et al. *J. Clin. Microbiol.* 32:1333-1337 (1994), each incorporated by reference herein).

Diarrheal stools of study subjects were examined for ova and parasites, and they were tested for salmonella, shigella, campylobacter, aeromonas, yersinia, enterovirus, adenovirus, and rotavirus. Diarrheal stools were also examined by electron microscopy for rotavirus and other viral particles. To detect adventitious agents associated with intercurrent illness, nasal swabs or nasal wash specimens were collected from study subjects who had fever and respiratory symptoms during the 7-day observation period in studies of P×UK and ST3×UK reassortants, and these specimens were tested in cell culture for respiratory viruses.

The rates of illness of vaccinees and placebo recipients and the rates of serologic response for these groups within each age group and in each study were compared using a two-tailed Fisher's exact test.

The percentages of adults, children and infants who had rotavirus detected in their stools or developed a fourfold or greater rise in serum antibody titer(s) after a single oral administration of each of the VP7-serotype-specific human× UK bovine rotavirus reassortants are shown in Table 1. Rotavirus was not recovered in cell culture from the stools of any of the adult vaccinees, infants <6 months old fed undiluted P×UK reassortant, or placebo recipients. Only a small proportion of (i) the children 6-60 months old given a 1:10 dilution of the D×UK, DS-1×UK or P×UK reassortant or (ii) the infants under 6 months of age administered an undiluted dose of the D×UK or DS-1×UK strain shed rotavirus. In most cases rotavirus was detected after the second cell culture passage of only one or two stool samples. In contrast, the ST3×UK virus was recovered from stools of the infants and young children more frequently and for a longer period (usually stools collected over a period of 3 or more days, especially during days 5-7 postvaccination). The ST3×UK virus was isolated from the stool of one 23-month-old child on day 30 postvaccination and confirmed by PCR. Quantitation of the virus recovered from stools of nine ST3×UK rotavirus reassortant recipients indicated the maximum amount of virus shed was $4.7 \times 10^2$ plaque forming units (pfu) per ml of the 10% stool suspension.

Tests by PCR of 10% stool suspensions (9 of 9) or tissue culture passages of stools (1 of 1) from ten vaccine recipients confirmed the shedding of the ST3×UK rotavirus reassortant in all ten vaccinees. However, three of these vaccinees also shed a wild-type rotavirus: a VP7 serotype 1 human rotavirus strain (one infant) or a VP7 serotype 3 strain (one child and one infant). Data from these three pediatric patients, who did not have rotavirus-like illness, were excluded from the serologic analysis.

Serologic responses to rotavirus were detected less often in adults and older children (who probably had been infected with wild-type rotavirus previously) than in young infants (Table 1). Serologic responses were detected in 23%, 18% and 15% of the adults who were fed the D×UK, DS-1×UK or ST3×UK reassortant, respectively, but in none of the adults inoculated with the P×UK reassortant. Among the children 6-60 months-old who received a 1:10 dilution, serologic responses to rotavirus were detected in 33% of D×UK recipients. 40% of DS-1×UK recipients, and 57% of ST3×UK recipients. The $10^{4.1}$ pfu dose of P×UK reassortant failed to elicit any antibody responses in children between 6 and 60 months of age, but a ten-fold higher dose of this composition was moderately immunogenic, with antibody responses detected in 5 of 11 (45%) children in this age group who were given this reassortant orally.

neutralizing antibodies against the UK bovine rotavirus parent strain (data not shown) or the DS-1×UK reassortant at a rate of 55% and 82%, respectively, whereas none of them developed a significant increase in neutralizing antibodies to the DS-1 human rotavirus parent strain.

This absolute dissociation of VP7 and VP4 responses was not the rule, however, because infant vaccinees who received a single dose of the type 1(D) human×bovine rotavirus reassortant developed a VP7-specific neutralizing antibody response to the human rotavirus serotype 1 parent in 50% of instances. In addition, a homotypic VP7 neutralizing antibody response was also observed, albeit at a lower frequency, for human rotavirus type 3 (10%) and type 4 (8%). It should be noted that, as in Example II for the quadrivalent formulation infra, immunogenicity of the human×bovine rotavirus reassortants was considerably greater when three sequential doses of the reassortants were administered at two month intervals. Thus, this expanded immunization schedule induced a VP7-specific neutralizing antibody response to each of the human rotavirus parents of the reassortants that in the case of serotypes 2, 3, and 4 significantly exceeded the response observed following a single dose of reassortant. Specifically. 32% of infant vaccinees responded to serotype 2. 33% to serotype 3 and 42% to serotype 4. Improvement was not noted for serotype 1 where immunogenicity was already high after a single dose of this reassortant.

There was no evidence that rotavirus was shed in stools of placebo recipients, nor was there evidence for a rotavirus

TABLE 1

Virologic and serologic responses of infants, children and adults following a single dose of human VP7 serotype-specific-bovine UK rotavirus reassortant vaccines

| Age Group Vaccine Strain | Dose Given ($\log_{10}$pfu) | No. of subjects | % Infected | % Who Shed Rotavirus | Plaque Reduction Neutralization | | ELISA | | Any Assay |
|---|---|---|---|---|---|---|---|---|---|
| | | | | | Vaccine-Strain | Human Rotavirus Parent | IgA | IgG | |
| *Infants, 1.5-5.9 months* | | | | | | | | | |
| D x UK | 4.8 | 8 | 63 | 38 | 50 | 50 | 63 | 38 | 63 |
| D x UK | 5.8 | 20 | 50 | 15 | 30 | 30 | 40 | 35 | 50 |
| DS-1 x UK | 4.3 | 8 | 63 | 0 | 38 | NT | 38 | 50 | 63 |
| DS-1 x UK | 5.3 | 11 | 82 | 18 | 82 | 0 | 18 | 18 | 82 |
| P x UK | 5.3 | 10 | 80 | 10 | 70 | 10 | 10 | 10 | 80 |
| ST3 x UK | 5.8 | 14 | 93** | 64 | 92 | 9† | 25 | 44 | 92 |
| *Children, 6-60 months* | | | | | | | | | |
| D x UK | 4.8 | 9 | 33 | 11 | 22 | 33 | 11 | 11 | 33 |
| DS-1 x UK | 4.3 | 10 | 40 | 10 | 40 | NT | 40 | 40 | 40 |
| P x UK | 4.3 | 10 | 10 | 10 | 0 | NT | 0 | 0 | 0 |
| P x UK | 5.3 | 11 | 45 | 0 | 36 | NT | 9 | 27 | 45 |
| ST3 x UK | 4.8 | 8 | 63** | 63 | 43 | 17† | 43 | 57 | 57 |
| *Adults, 18-45 years* | | | | | | | | | |
| D x UK | 5.8 | 13 | 23 | 0 | 8 | 8 | 15 | 8 | 23 |
| DS- I x UK | 5.3 | 11 | 18 | 0 | 9 | NT | 9 | 18 | 18 |
| P x UK | 5.3 | 12 | 0 | NT | NT | NT | 0 | 0 | 18 |
| ST3 x UK | 5.8 | 20 | 15 | 0 | 0 | 0 | 10 | 10 | 15 |

Note:
pfu — plaque forming units;
NT = not tested.
Infection was defined as evidence of virus shedding of a fourfold or greater rise in titer of serum rotavirus-specific antibody measured by ELISA IgA or IgG assay or plaque reduction neutralization assay.
*The rotavirus vaccine and human rotavirus strains used in plaque reduction neutralization assays were D x UK and Wa; DS-1 x UK and DS-1; P x UK and P; and ST3 x UK and ST3 strains.
†Serum specimens from one infant and two children were not tested.
** One child and two infants who shed rotavirus reassortant who had evidence of wild-type rotavirus in their stool by PCR analysis. The serologic results of these three vaccinees were excluded from the analysis of antibody responses.

Among infants <6 months of age who were fed rotavirus, serologic responses, (a measure of immunogenicity), were detected more often (93%) in recipients of an undiluted dose of human×bovine UK reassortant derived from the ST3 human rotavirus strain than in those who received a 1:10 or undiluted dose of the human×bovine UK reassortants derived from the D (50-63%), DS-1 (82%), or P (63-80%) human rotavirus strain. These differences with regard to dose were not statistically significant. Overall, antibody responses were detected more often by plaque reduction neutralization (PRN) assay (using the homologous reassortant virus as antigen) than by the ELISA IgA or IgG assay (using rhesus rotavirus as a group-specific antigen) in all vaccine groups except for the D×UK vaccine group in which antibody responses were detected most often by the IgA ELISA. For three of the reassortants, the neutralizing antibodies in the postimmunization sera of the vaccinated infants were directed more often against the reassortant rotavirus than the human rotavirus parent strain, suggesting that the VP4 neutralization antigen of the bovine rotavirus was immunodominant. This was particularly evident in the results of PRN tests on postimmunization sera of 11 infants who were fed $10^{5.3}$ pfu of DS-1×UK and who developed a significant increase in serologic response in this group with the exception of one 6-month-old placebo recipient who had a four fold rise in titer of ELISA IgG antibody, but no other serologic response in the other assays.

Each of the rotavirus reassortants appeared to be safe and well tolerated, as evidenced by the absence of gastrointestinal illness in adults, and the lack of a statistically significant increase in the rate of "rotavirus-like illnesses" between pediatric vaccinees and placebo recipients in each vaccine group and age group (Table 2). Only three adult volunteers (recipients of P×UK or ST3×UK vaccine) had any symptoms (fever) that met the criteria for "rotavirus-like illness;" however, none of these ill vaccinees had evidence of rotavirus infection. All three adults who developed a fever following administration of rotavirus had a concomitant respiratory illness or shed a respiratory virus that was detected by tissue culture assay of a nasopharyngeal swab. One P×UK recipient with volunteers suggest that these fevers probably were due to an intercurrent respiratory tract infection.

Intercurrent illness also occurred during most of the studies of the four rotavirus vaccine candidates in pediatric subjects. Vomiting in association with coughing, and fever associated with otitis media or respiratory symptoms were common. Despite the high background of intercurrent illnesses, the rate of "rotavirus-like illnesses" (fever, diarrhea or vomiting) in 6-60 month-old children and infants <6 months of age within each vaccine group was not statistically significantly different from that of the placebo recipients (Table 2). Overall, 8 of 48 children 6-60 months old who were given a reassortant rotavirus, and 3 of 27 recipients of the placebo experienced "rotavirus-like illness" within 7 days after inoculation. Only two of these rotavirus-like illnesses were associated with rotavirus infection. Both illnesses, which occurred after oral administration of the DS-1×UK reassortant, were mild and self-limited: one child had fever (maximum, 38.5° C.) on day 2; the other child vomited three times on days 2 and 3.

TABLE 2

Frequency of illness in adults and infants after oral administration of human VP7 serotype-specific bovine UK rotavirus reassortant vaccines, or placebo.

| Vaccine Evaluated, Age Group | Dose of Vaccine ($\log_{10}$ pfu) or Placebo | Administered Vaccine/Placebo | % Infected | % of Subjects with Indicated Findings | | | | | |
|---|---|---|---|---|---|---|---|---|---|
| | | | | Fever | Diarrhea | Vomiting | Any Rotavirus-like Illness | Respiratory Illness or Otitis Media | ALT Elevation* |
| D × UK | | | | | | | | | |
| 18-40 yrs. | 5.8 | 13 | 23 | 0 | 0 | 0 | 0 | 0 | 15 |
| 18-40 yrs. | 0 | 8 | 0 | 0 | 0 | 0 | 0 | 0 | 0 |
| 6-60 mos. | 4.8 | 9 | 33 | 11 | 0 | 11 | 22 | 22 | 0 |
| 6-60 mos. | 0 | 5 | 0 | 0 | 20 | 0 | 20 | 0 | 20 |
| 1.5-5.9 mos. | 4.8 | 8 | 63 | 13 | 0 | 0 | 13 | 13 | 0 |
| 1.5-5.9 mos | 0 | 6 | 0 | 0 | 17 | 0 | 17 | 17 | 0 |
| 1.5-5.9 mos. | 5.8 | 20 | 50 | 30 | 15 | 30 | 50 | 15 | 0 |
| 1.5-5.9 mos. | 0 | 10 | 0 | 10 | 20 | 20 | 30 | 0 | 0 |
| DS-1 × UK | | | | | | | | | |
| 18-40 yrs. | 5.3 | 11 | 18 | 0 | 0 | 0 | 0 | 0 | 0 |
| 6-60 mos. | 4.3 | 10 | 40 | 20 | 0 | 20 | 30 | 20 | 0 |
| 6-60 mos. | 0 | 6 | 13 | 33 | 0 | 0 | 33 | 17 | 0 |
| 1.5-5.9 mos. | 4.3 | 8 | 63 | 13 | 0 | 13 | 25 | 25 | 0 |
| 1.5-5.9mos. | 0 | 4 | 0 | 0 | 0 | 0 | 0 | 0 | 0 |
| 1.5-5.9 mos. | 5.3 | 11 | 82 | 9 | 18 | 27 | 45 | 9 | 0 |
| 1.5-5.9 mos. | 0 | 4 | 0 | 25 | 0 | 25 | 50 | 25 | 0 |
| P × UK | | | | | | | | | |
| 18-40 yrs. | 5.3 | 12 | 0 | 17 | 0 | 0 | 17 | 8 | 0 |
| 6-60 mos. | 4.3 | 10 | 10 | 20 | 0 | 10 | 20 | 10 | 0 |
| 6-60 mos. | 0 | 5 | 0 | 0 | 0 | 0 | 0 | 40 | 0 |
| 6-60 mos. | 5.3 | 11 | 45 | 0 | 0 | 0 | 0 | 0 | 0 |
| 6-60 mos. | 0 | 6 | 0 | 0 | 0 | 0 | 0 | 0 | 0 |
| 1.5-5.9 mos. | 5.3 | 10 | 80 | 0 | 0 | 0 | 0 | 0 | 0 |
| 1.5-5.9 mos. | 0 | 5 | 0 | 20 | 0 | 20 | 20 | 0 | 0 |
| ST3 × UK | | | | | | | | | |
| 18-45 yrs. | 5.8 | 20 | 15 | 5 | 0 | 0 | 5 | 25 | 0 |
| 6-60 mos. | 4.8 | 8 | 63 | 13 | 0 | 0 | 13 | 25 | 0 |
| 6-60 mos. | 0 | 5 | 0 | 0 | 0 | 0 | 0 | 80 | 0 |
| 1.5-5.9 mos. | 5.8 | 14 | 93 | 21 | 7 | 14 | 36 | 57 | 7 |
| 1.5-5.9 mos. | 0 | 7 | 0 | 0 | 0 | 14 | 14 | 14 | 14 |

Note:
Rotavirus-like illness was defined as the presence of fever, diarrhea or vomiting, as defined in the methods section.
*Results were based on ALT levels measured in blood collected 4-6 after inoculation.

sinusitis, cough and rhinorrhea had a positive culture for influenza A virus; another P×UK recipient had a positive culture for respiratory syncytial virus (RSV); and one ST3× UK recipient had cough, rhinorrhea and hoarseness. The concomitant respiratory illnesses, recovery of respiratory pathogens and lack of evidence of rotavirus infection in these Coxsackie B5 or an echovirus and cytomegalovirus were isolated from two children 6-60 months old who were fed ST3×UK. Also, an adenovirus or parainfluenza type 3 virus was isolated from three placebo recipients in the same study.

Among study subjects <6 months of age, 23 of 71 vaccine recipients and 8 of 36 placebo recipients experienced "rotavirus-like illness" within 7 days after the oral administration of the first dose of rotavirus reassortant. Fever in infants without respiratory symptoms or otitis media was lower (range, 38.2-38.3° C.) than in those with respiratory symptoms or otitis media (range, 38.4-40° C.). The majority (8 of 12) of infants who vomited had only one or two episodes; none had vomiting that interfered with feeding or resulted in dehydration. The rates of "rotavirus-like illness" and respiratory tract illness or otitis media in infants (classified as infected vaccinees, uninfected vaccinees or placebo recipients) are shown in Table 3. Infected vaccinees were vaccine recipients who had evidence of rotavirus infection after vaccination; uninfected vaccinees were vaccine recipients in whom there was no evidence of rotavirus infection after vaccination. There was no consistent pattern of symptoms among infected vaccinees, nor were there significant differences between the rates of illnesses in infected vaccinees and uninfected vaccinees or placebo recipients for each vaccine group. Suggesting that the observed symptoms were manifestations of intercurrent illness as elaborated below.

Among the <6 months-old vaccinees with rotavirus-like illness. 14 were vaccine responders. All but three of the vaccine responders had mild rotavirus-like illnesses with one or two symptoms; two had fever alone; three had fever with respiratory illness or otitis media; nine vomited one or more times (maximum 6 times) and three of them vomited after coughing. Three vaccine responders had moderate-to-severe "rotavirus-like illness" following feeding of $10^{5.8}$ pfu of ST3×UK, but they also had an intercurrent respiratory virus infection. Adenovirus and cytomegalovirus were isolated from nasal wash specimens. In addition, the appropriate rotavirus reassortant was recovered from the stools of one child who developed high fever (maximum, 40° C.) for 3 days, but this child also had rhinorrhea, cough, and otitis media for 5 days. This child was hospitalized and treated empirically with vancomycin and cephalosporin until sepsis was ruled out; she recovered uneventfully. Parainfluenza virus and adenovirus were cultured from nasal specimens of one infant with fever (maximum, 39.3° C.) and otitis media for two days: this child also shed the appropriate rotavirus reassortant in stools. Influenza A virus (but not rotavirus) was isolated from another infant with fever (maximum, 38.6° C.), diarrhea (9 watery stools) over 3 days, and wheezing, cough and rhinorrhea for 3-4 days.

TABLE 3

Illness and adventitious agents identified in infants <6 months-old who were infected or not infected with a human-bovine UK reassortant rotavirus vaccine or who received placebo.

Percentage of Subjects with

| Reassortant Virus Evaluated, Subjects (no.) | Fever >38.1* | Vomiting | Diarrhea | "Rotavirus-like Illness" | Respiratory Illness or Otitis Media | Adventitious Agents Identified (no. of subjects) |
|---|---|---|---|---|---|---|
| D x UK | | | | | | |
| Infected vaccinees (14) | 14 | 36 | 7 | 36 | 7 | — |
| Uninfected vaccinees (14) | 36 | 7 | 14 | 43 | 21 | Aeromonas hydrophilia (1) |
| Placebo (16) | 6 | 13 | 19 | 25 | 6 | — |
| DS-1 x UK | | | | | | |
| Infected vaccinees (14) | 0 | 21 | 7 | 29 | 14 | — |
| Uninfected vaccinees (5) | 40 | 40 | 20 | 60 | 20 | Campylobacter jejuni (1) |
| Placebo (8) | 13 | 13 | 0 | 25 | 13 | — |
| P x UK | | | | | | |
| Infected vaccinees (8) | 0 | 0 | 0 | 0 | 0 | |
| Uninfected vaccinees (2) | 0 | 0 | 0 | 0 | 0 | — |
| Placebo (5) | 20 | 20 | 0 | 20 | 0 | |
| ST3 x UK | | | | | | |
| Infected vaccinees (13) | 23 | 15 | 8 | 38 | 62 | RSV (2), parainfluenza (1); adenovirus (2), CMV (1); influenza (1) |
| Uninfected vaccinees (1) | 0 | 0 | 0 | 0 | 0 | — |
| Placebo (7) | 0 | 14 | 0 | 14 | 14 | RSV (1) |

Note:
Infants were considered infected with the rotavirus reassortant virus administered if they shed rotavirus and/or had a fourfold or greater increase in serum rotavirus-specific antibody titer. Rotavirus-like illness was defined as fever, vomiting or diarrhea.
RSV = respiratory syncytial virus;
CMV = cytomegalovirus.

As shown in Table 3, nine of 22<6 months-old vaccinees who had no evidence of rotavirus infection experienced "rotavirus-like illness." Campylobacter jejuni was isolated from one infant who had fever and 34 dysenteric stools after receiving $10^{5.3}$ pfu of DS-1×UK. Aeromonas hydrophila was isolated from diarrheal stools of another infant who also had fever and otitis media after receiving $10^{5.8}$ pfu of D×UK. Respiratory syncytial virus was also isolated from two infants who received the D×UK reassortant as well as from one placebo recipient, each of whom had rhinorrhea with or without wheezing.

There was no evidence of liver damage resulting from infection with the rotavirus reassortants. The proportion of pediatric participants with an ALT elevation 4-6 weeks postinoculation was no greater in vaccinees than in placebo recipients. Only two pediatric vaccinees (one infant vaccinated once with ST3×UK and another who received a second dose of D×UK) had an elevated ALT value. This value was less than twice normal and was normal when repeated within a week. Two placebo recipients also had mildly elevated ALT values 4-6 weeks postinoculation. Transient, mild elevations in ALT values were occasionally detected in adult volunteers (some of whom reported alcohol consumption) after feeding of the D×UK or ST3×UK reassortant. None of these volunteers had evidence of rotavirus infection. Four adults had ALT elevations one week after administration of D×UK; their ALT levels were normal or less than twice the normal value (two volunteers) when repeated three weeks later. Two other adults had an elevated ALT level one week after receiving the ST3× UK reassortant; their ALT values were normal 4 weeks after administration of rotavirus.

Although only 10 of 20 (50%) infants who received $10^{5.8}$ pfu of D×UK reassortant rotavirus developed rotavirus-specific antibodies after one dose, a booster immunization of 14 infants with this reassortant 4-12 weeks later elicited a fourfold or greater increase in antibody titer in 12 of the 14 (86%) infants, including 7 infants who had mounted an antibody response after the first dose. Among the 14 infants who received both doses, the net effect of the second dose was to elicit antibodies in all 14 vaccinees and to boost the level of neutralizing antibodies against the rotavirus reassortant, from a geometric mean titer of 1:66 after the first dose, to 1:336 after the second dose.

After booster immunization with D×UK, only one rotavirus reassortant recipient shed rotavirus and this was for only one day after which virus could not be recovered from the child. Only two of the 14 infants (five of whom had not been infected after the first dose) experienced rotavirus-like illness after the second dose. One child, who had not been infected with the rotavirus reassortant after the first dose, had mild fever (maximum 38.1° C.) along with rhinorrhea after the second dose. Another child, who had been infected by the reassortant virus after the first dose, vomited 4 times after receiving the second dose. One of the vaccinees in this group had an elevated ALT value after the booster dose, which was normal when repeated.

Example II

This example describes a quadrivalent human×bovine reassortant rotavirus immunogenic composition that was evaluated for its clinical safety and immunogenicity in adults, young children, and infants.

The four human×bovine reassortant rotaviruses described in Example I were combined in equal volumes to form a single quadrivalent vaccine composition. All studies were conducted in a placebo-controlled manner to assess the safety and immunogenicity of the combined composition. All serologic and microbiological testing were carried out as described in Example I.

A single dose of undiluted quadrivalent human (VP7 serotypes 1, 2, 3, and 4)-bovine UK rotavirus vaccine containing $10^{5.3}$ to $10^{5.8}$ PFU per reassortant was evaluated in 17 adults (11 vaccine recipients and 6 placebo recipients) at the Johns Hopkins University Center for Immunization Research. Study subjects fasted for at least one hour before and after administration of vaccine or placebo. They were fed 120 ml of a buffer solution (sodium bicarbonate) to neutralize gastric acidity followed one minute later by the quadrivalent immunogenic composition mixed with the buffer, or the placebo. One of the 11 adult vaccinees reported a single episode of vomiting and three diarrheal stools during days 2 and 3 and pharyngitis and rhinorrhea between days 4 and 5 postvaccination. This volunteer had no evidence of rotavirus infection, his stools were negative for rotavirus by culture and electron microscopic examination, and a serologic response to rotavirus was not detected. Bacterial cultures of the diarrheal stools were also negative. The other 10 vaccinees and 6 placebo recipients were asymptomatic postvaccination. None of the vaccine or placebo recipients had an elevated ALT postvaccination, nor was rotavirus detected in their stools. Rotavirus antibody responses were detected in sera of 6 (55%) of eleven vaccinees (5 by ELISA IgA assay and 4 by ELISA IgG assay). Thus, the quadrivalent vaccine appeared to be safe and immunogenic enabling further evaluation in children 6 to 60 months of age.

During a subsequent study, twenty infants and children 6 to 60 months of age were fed a buffered formula followed by a single dose of undiluted quadrivalent human VP7 serotype 1×UK, human VP7 serotype 2×UK, human VP7 serotype 3×UK, and human VP7 serotype 4×UK rotavirus reassortant vaccine (12 children) or placebo (8 children) at least two weeks before or after receiving routine childhood immunizations appropriate for the individual's age. "Rotavirus-like illness" was observed in one vaccinee (fever during the first 24 hours after receiving virus and one episode of vomiting on day 4) and in one placebo recipient (fever on day 2 as well as rhinorrhea and cough on days 2-7). Another vaccinee had rhinorrhea on day 7. None of the ill children demonstrated evidence of rotavirus infection. Rotavirus was only detected in two stool specimens collected from two asymptomatic vaccinees on a single day. Rotavirus was not detected by electron microscopy or by culture of stools of the other vaccinees or placebo recipients, including four children who were siblings of vaccine recipients. None of the vaccinees or placebo recipients had an ALT elevation after administration of the quadrivalent rotavirus preparation. Rotavirus antibody responses were detected in 6 of 12 vaccinees (4 by ELISA IgA assay and 6 by ELISA IgG assays). Altogether 7 of 12 vaccinees had evidence of rotavirus infection. Thus, the candidate vaccine appeared to be safe and immunogenic, enabling progression to the target population of infants of less than six months of age who received three doses of vaccine.

The safety and immunogenicity of three doses of the undiluted quadrivalent human×bovine rotavirus reassortant vaccine or placebo was next evaluated in 30 young infants who received their routine pediatric immunizations concurrently at approximately 2, 4, and 6 months of age. Twenty infants were randomized to receive the candidate rotavirus vaccine and ten infants to receive placebo. One vaccinee and one placebo recipient were withdrawn from the study prior to the second vaccination for medical reasons. After the first, second or third dose of vaccine or placebo along with routine childhood immunizations (including whole cell pertussis vaccination), fever was reported in 1 of 20, 6 of 19, and 6 of 19 vaccinees, and in 2 of 10, 0 of 9, and 3 of 9 placebo recipients, respectively. All episodes of fever occurred within the first 48 hours after oral administration of the quadrivalent rotavirus formulation that coincided with multiple routine pediatric immunizations, except for three febrile episodes, two of which were accompanied by respiratory illness in vaccinees while the third episode occurred in a placebo recipient. Diarrhea was reported in one placebo recipient, but not in any vaccinee. One vaccinee had two episodes of vomiting, as well as respiratory symptoms and conjunctivitis, on day 7 after the second dose. Another child had a single episode of vomiting precipitated by coughing during the first 24 hours after vaccination. Only one vaccinee with mild fever (38.2° C.) had rotavirus detectable in a stool sample, suggesting that the fever was associated with rotavirus infection. Respiratory symptoms or rashes were seen in 4 of 19 vaccinees after the second and after the third doses, and in 1 of 10 placebo recipients after the first dose and in 1 of 9 placebo recipients after the second and third doses. All illnesses reported were mild. ALT was slightly elevated before and after the first vaccination in 5 of 20 and 2 of 20 vaccinees, respectively, and in 1 of 10 and 2 of 10 placebo recipients. Rotavirus was detected in stools by tests in cell culture for 2 of 20 vaccinees after the first dose, in 0 of 19 vaccinees after the second dose, as well as 2 of 19 vaccinees after the third dose.

Based on evidence of rotavirus shedding and/or a virus-specific serum antibody response, 12 of 19 (63%) vaccinees were infected with rotavirus after receiving the first dose and 19 of 19 (100%) after receiving three doses. (Sera were not collected after the second vaccination). Only a few infants had rotavirus detected in their stools that were collected on days 3, 5 and 7 after the first dose and on day 4 after the second and third doses. Specifically, 3 of 20 (15%) shed rotavirus after the first dose of vaccine and 1 of 19 (11%) after the third dose. Neither of the two infants (one vaccinee and one placebo recipient) who were withdrawn from the study because of an elevated ALT before and after the first dose had any evidence of rotavirus infection. Among the 19 vaccinees who received 3 doses of vaccine, antibody responses were detected by the following assays following the first and/or third dose of vaccine: ELISA IgA (50%). ELISA IgG (63%), and plaque reduction neutralization assay against the UK bovine strain (100%) or human rotavirus type 1 (Wa, 32%), 2 (DS-1.32%), 3 (P. 32%), or 4 (VA70, 32%). (Table 4)

TABLE 4

Serologic Responses in Individuals who Received Three Doses of Approximately $4 \times 10^5$ PFU of Quadrivalent Bovine (UK) Rotavirus-based Vaccine or Placebo in Infants Vaccinated at Approximately 2,4 and 6 Months of Age

| | No. with 4-fold or greater serum antibody response[a] | | | | | |
|---|---|---|---|---|---|---|
| | by | by neutralization versus indicated virus/no. tested | | | | |
| Group | ELISA IgA* / IgG* | Wa (1)** | DS-1 (2) | P (3) | VA-70 (4) | UK (6) |
| Vaccine | 9/18/12/29 (50%)/(63%) | 8/19 (42%) | 6/19 (32%) | 6/19 (32%) | 6/19 (32%) | 19/19 (100%) |
| Placebo | 0/8/1/9 | 0/9 | 0/9 | 0/9 | 0/9 | 0/9 |

[a]Following first and/or third dose
*Rotavirus group specific response
**VP7 Serotype At the conclusion of the study, 7 placebo recipients aged 8.25 to 9.25 months were given a single dose of the quadrivalent rotavirus vaccine. This vaccine appeared to be well tolerated. Rotavirus-like illness was observed in only one infant who had a fever on days 3, 4 and 7 as well as rhinorrhea on days 3 through 7. Respiratory illness (without fever or gastroenteritis) was observed in 5 other vaccinees. The absence of significant development of fever for the bovine UK rotavirus-based vaccine in this older age group is of considerable importance because a monovalent rhesus rotavirus vaccine had been shown to be considerably more prone to induce a febrile response in infants 6 to 8 months of age, a time when most, if not all, passively acquired maternal antibodies to rotavirus have been lost.

When these serologic responses to the bovine UK-based quadrivalent composition were compared to the neutralizing antibody responses induced in infants vaccinated at 2, 4, and 6 months of age with the rhesus rotavirus-based quadrivalent vaccine administered at $10^{5.0}$ pfu of each component (Rennels et al., *Pediatrics* 97:7-13 (1996)), several important features were noted. The neutralizing antibody responses induced by the rhesus rotavirus-based vaccine included a response to rhesus rotavirus, one of the parent strains of the reassortants, in 90% of the infants vaccinated. Also, a neutralizing antibody response was induced to human rotavirus serotype 1 in 14% of the children, to human serotype 2 in 31%, to human serotype 3 in 29%, and to human serotype 4 in 14%. Therefore, the bovine UK rotavirus-based human reassortant immunogenic composition induced a significantly greater frequency of neutralizing antibody responses to serotype 1 (P<0.005 Fisher exact test) and to serotype 4 (P<0.05 Fisher exact test) than the rhesus rotavirus tetravalent composition. Responses to human rotavirus serotype 2 and 3 strains and the homotypic animal rotavirus parental strain were not significantly different.

The equivalence and possible superiority of immunogenicity of the tetravalent human×bovine UK rotavirus reassortant vaccine when compared to the human×rhesus rotavirus reassortant vaccine assumes significance when viewed in the context of the high level of protective efficacy conferred by the rhesus rotavirus-based vaccine.

In a multicenter efficacy trial in the United States, the rhesus rotavirus vaccine was demonstrated to have a protective efficacy of 80% against very severe rotavirus diarrhea and 100% efficacy against dehydration caused by rotavirus (Rennels et al. *Pediatrics* 97:7-13 (1996)). This vaccine was licensed by the Food and Drug Administration in August 1998 after its clinical profile had been approved by the FDA Advisory Committee in December 1997. This vaccine was recommended for routine immunization of infants at 2, 4, and 6 months of age by the U.S. Advisory Committee for Immunization Practices in June 1997, pending licensure. On May, 1999, it was licensed in the fifteen countries of the European community.

The bovine UK rotavirus-based multivalent immunogenic composition does not appear to induce a transient low level fever in humans. A bovine UK rotavirus-based multivalent composition might be preferred in some clinical situations. Thus, the bovine UK rotavirus-based multivalent immunogenic compositions of the present invention provide a unique constellation of properties including (1) infectivity and immunogenicity similar to the licensed quadrivalent rhesus rotavirus vaccine; (2) reduced ability to induce a transient low level fever; (3) attenuation similar to that previously described for bovine rotavirus-based vaccine compositions, but with significantly greater infectivity and immunogenicity as judged from the lower dosage required; and (4) antigenic coverage for all of the human rotavirus serotypes of major clinical importance in severe rotaviral disease.

Example III

In this example a summary is provided of a preliminary interim analysis of data from an ongoing clinical trial that allowed a comparison of a preferred tetravalent human-bovine reassortant rotavirus composition of the present invention with the licensed tetravalent rhesus-human rotavirus reassortant vaccine. ROTASHIELD. The analysis examined the rate of low level fever response and the protective efficacy against rotaviral diarrhea of the two compositions.

The interim two year clinical study is currently in progress to compare a tetravalent human-bovine rotavirus composition of the present invention with the tetravalent rhesus-human rotavirus reassortant vaccine (ROTASHIELD, recently licensed for use in the United States and the 15 countries of the European Community) for safety and protective efficacy against rotaviral diarrhea. The study is being performed in Finland and includes 172 tetravalent human-bovine rotavirus reassortant recipients, 86 corresponding placebo controls, 161 ROTASHIELD vaccinees and 79 corresponding placebo recipients. For logistical reasons the study was performed in two adjacent small Finnish cities, Tampere and Lahti and therefore it was necessary to employ two placebo groups. Two placebo groups were also required when individuals in both study groups were in the same location, because the containers for the compositions differed in appearance.

The study was established to run concurrently in both cities in order to recruit sufficient study subjects for each composition that could detect with 80% power a decreased incidence (from 30% to 15%) of a febrile response to a composition (assuming an insignificant difference between placebo groups, a two-tailed test at 0.05 significance level and 10% dropouts). The tetravalent human-bovine rotavirus reassortant composition and its corresponding placebo were randomized only in Tampere, whereas, the ROTASHIELD vaccine and its corresponding placebo were randomized in both Lahti and Tampere.

For each composition dose, study subjects were monitored for 7 days post immunization for fever, defined as a rectal temperature equal to or greater than, 38° C. Monitoring was also maintained for episodes of vomiting, loose stools, irritability and other systemic events during the 7 days following immunization. Monitoring for gastroenteritis, serious adverse events, or hospitalization was to be maintained for the entire term of the two year study. The study was planned to include two seasons of gastroenteritis.

Preliminary data has been obtained on the rate of a febrile response following the first dose of each tetravalent reassortant composition or placebo without unblinding members of the study team. Further, only data for each group, as a whole, has been analyzed to compare the two compositions, i.e., the tetravalent human-bovine rotavirus reassortant composition and ROTASHIELD, for occurrence of fever and for protective efficacy. Comparability between the study groups was maintained with respect to the cell culture substrate by formulating both compositions to contain rotavirus grown in qualified diploid simian fetal rhesus lung (FRhL) cells.

Following randomization, the tetravalent human-bovine rotavirus reassortant composition ($10^{5.3}$ to $10^{5.8}$ pfu per component), ROTASHIELD ($10^5$ pfu per component), or placebo was administered orally to healthy 2 month old infants and again 2 months later. Parents of the infants recorded rectal temperatures once, or twice a day, and symptoms were recorded daily. Stool samples were collected and a record of the number and consistency of the stools passed was maintained. Available data summarizing cumulative rates of fever occurring during the seven day period following the first dose of rotavirus reassortant composition and preliminary data summarizing protective efficacy during the first season of rotaviral gastroenteritis are provided in Table 5 and Table 6 and summarized below.

Among the ROTASHIELD recipients, 46.2% developed a low level transient febrile response (≧38° C. (100.4° F.)) during the week following administration of the first dose of reassortant composition (Table 5). This frequency was significantly greater than that of its placebo group whose rate of fever was 11.4% ($p<0.0001$). In contrast, the rate of fever (≧38° C.) observed for the tetravalent human-bovine rotavirus reassortant composition recipients (15.2%) did not differ significantly from that of its placebo group (11.0%). The frequency of a fever of >38.4° C. (101.1° F.) for the ROTASHIELD vaccinees was still appreciable (20.3%) and was significantly greater ($p<0.0001$) than that of its placebo group (1.3%). In contrast, the frequency of fever of >38.4° C. experienced by recipients of the tetravalent human-bovine rotavirus reassortant composition was 1.8%, which was not significantly different from that of its placebo group (0%). Thus, in these two comparisons, ROTASHIELD induced fever with an appreciable frequency that was significantly higher than that of its placebo group, whereas febrile response to the tetravalent human-bovine rotavirus reassortant composition did not differ from that of its placebo and was significantly less than observed for ROTASHIELD. Overall, ROTASHIELD was associated with significantly more fever during the seven days following immunization than was the tetravalent human-bovine rotavirus reassortant composition, ($p<0.0001$), whether fever was defined as ≧38° C. or >38.4° C. The essentially total lack of a febrile response to the human×bovine reassortant composition in the Finnish trial is reflective of the absence of background illnesses in the study group. This is in sharp contrast to Examples I and II where background illnesses were quite frequent. In the Finnish study, the relative absence of background illness allowed the evaluation of the development of fever, or a febrile response with greater precision than was possible in the earlier clinical trials.

Preliminary data was also obtained relating to the comparative protective efficacy against rotavirus diarrhea of the tetravalent human-bovine rotavirus reassortant composition and ROTASHIELD. This data was particularly important because with the lack of observed febrile response of the former composition and the use of a 10 to 100-fold lower virus dose than had been used for the previous bovine rotavirus and human-bovine reassortant compositions, it was conceivable that the current composition would be too attenuated to induce protection against naturally-occurring rotavirus illness. On the other hand, the human-rhesus rotavirus reassortant vaccine, ROTASHIELD, has characteristically been found to exhibit a protective efficacy of 80% to 100% against severe rotaviral disease.

An estimate for protective efficacy was obtained from the present study by analyzing the distribution of a total of 48 episodes of rotaviral gastroenteritis of any severity that were documented among the study subjects during the first season of surveillance. Diagnosis of rotaviral gastroenteritis was established by identification of rotavirus in the feces of a study subject with gastroenteritis. Identification was made by: (1) a standard immunological method, the ELISA technique, employing rotavirus group-specific and serotype-specific antisera (Joensuu et al. *Lancet* 350:1205-1209 (1997); and Hoshino et al. *J. Clin. Microbiol.* 21:425-430 (1985)), and (2) PCR employing primers that recognize rotavirus group-specific conserved sequences or rotavirus serotype-specific conserved sequences (Gouvea et al *J. Clin. Microbiol.* 28:276-282 (1990)).

Analysis of protective efficacy during the first season, was conducted in such a manner that the site study team, as well as the clinical and study monitoring staff, remained blinded to the assignment of individual subjects to a study group (i.e., tetravalent human-bovine rotavirus reassortant composition, ROTASHIELD, or corresponding placebo group) and they will remain blinded for the remaining term of the study. This restriction was applied to this preliminary analysis to permit continued surveillance and collection of data until the termination of the study at the finish of the second gastroenteritis season. As a consequence, the analysis of vaccine efficacy by severity of disease remains to be performed after the termination of the two year surveillance. Nevertheless, the rate of rotavirus gastroenteritis of any severity for each study group during the first season could be determined and compared to that of the other groups without unblinding the trial.

The rate of rotavirus gastroenteritis episodes of any severity for the two placebo groups during the first season was remarkably similar, 17.7% and 17.4%, indicating the comparability of the two study sites and of the epidemiology of rotavirus infection at these sites. When compared to its placebo group, ROTASHIELD exhibited a protective efficacy of 65% for rotavirus gastroenteritis of any severity. The comparable estimate for the tetravalent human-bovine rotavirus reassortant composition was 70%, a protective efficacy similar to the licensed vaccine. This level of protective efficacy was more than satisfactory considering the fact that efficacy could not be analyzed according to severity of disease. It is very likely that the protective effect of the human-bovine rotavirus reassortant composition against severe disease will be significantly greater than 70% based on the experience gained during previous ROTASHIELD clinical trials wherein rotavirus vaccine efficacy increased with increasing severity of disease. Characteristically with ROTASHIELD, a protective efficacy of 80% to 100% was observed for the most severe disease, while the protective efficacy calculated for any rotavirus illness of any severity reached only 48 to 68%.

TABLE 5

Cumulative Rates of Fever (Rectal) Occurring During the 7 Day Period Following First Dose of ROTASHIELD or Tetravalent Human-Bovine Reassortant Composition (TBRC) (Mean and 95% Confidence Interval (CI)).

| Rectal Temperature (° C.) | Group | No in Group | Subjects with Fever No. | Subjects with Fever Rate (%) | 95% CI (% 2 sided) | P Value for Indicated Comparison |
|---|---|---|---|---|---|---|
| ≧38 | ROTASHIELD[1] | 158 | 73 | 46.2 | 38.2-54.3 | <0.0001 |
|  | Placebo | 79 | 9 | 11.4 | 5.3-20.5 |  |
|  | TBRC[2] | 165 | 25 | 15.2 | 10-21.6 | <0.0001[a] |
|  | Placebo | 82 | 9 | 11 | 5.1-19.8 | NS |
| >38.4 | ROTASHIELD | 158 | 32 | 20.3 | 14.3-27.4 | <0.0001 |
|  | Placebo | 79 | 1 | 1.3 | 0-6.9 |  |
|  | TBRC | 165 | 3 | 1.8 | 0.4-5.2 | <0.0001[a] |
|  | Placebo | 82 | 0 | 0 | 0-4.4 | NS |
| >39.1 | ROTASHIELD | 158 | 3 | 1.9 | 0.4-5.3 | NS |
|  | Placebo | 79 | 0 | 0 | 0-4.6 |  |
|  | TBRC | 165 | 0 | 0 | 0-2.2 | NS |
|  | Placebo | 82 | 0 | 0 | 0-4.4 | NS |

[1] $10^5$ pfu per component of the tetravalent vaccine
[2] $10^{5.3}$-$10^{5.8}$ pfu per component of the tetravalent composition
NS = Not significant
[a] Comparison of occurrence of fever in ROTASHIELD vs TBRC groups

TABLE 6

Preliminary Report: A phase II Double Blind trial of the safety and immunogenicity of tetravalent human-bovine rotavirus reassortant composition and tetravalent rhesus rotavirus vaccine (ROTASHIELD). Distribution of first season rotaviral gastroenteritis illness of any severity by study group.

| Location | Study Group | No. of Subjects | No. who developed RV gastroenteritis of any severity (%) | Protective Efficacy |
|---|---|---|---|---|
| Lahti and Tampere | ROTASHIELD Placebo | 161 79 | 10 (6.2) 14 (17.7) | 65% (P < 0.02) |
| Tampere | TBRC Placebo | 172 86 | 9 (5.2) 15 (17.4) | 70% (P < 0.003) |

The vaccine of this invention exhibits all of the advantageous properties of the quadrivalent rhesus rotavirus formulation with regard to immunogenicity and protective efficacy. Similarly, the multivalent immunogenic compositions of the invention shares the advantageous property of lack of significant febrile response exhibited by the previously described bovine rotavirus formulations. However, it does not exhibit the disadvantageous features of the quadrivalent rhesus rotavirus vaccine regarding the development of transient low level febrile response or of the previously described bovine rotavirus formulations regarding their low infectivity.

Microorganism Deposit Information

The human rotavirus strains were deposited with the American Type Culture Collection, 10801 University Boulevard, Manassas, Va. 20110-2209, Jun. 4, 1998, under the conditions of the Budapest Treaty and designated as follows.

| Reassortant Designation | ATCC Accession Number |
|---|---|
| HD x BRV, clone 47-1-1 (VP7:l [D]) | ATCC VR-2617 |
| HDS1 x BRV-1, clone 66-1-1 (VP7:2 [DS-1] | ATCC VR-2616 |
| HP x BRV, clone 22-1-1 (VP7:3 [P]) | ATCC VR 2611 |
| HST3 x BRV-2, clone 52-1-1 (VP7:4 [ST3]) | ATCC VR-2612 |
| IAL28 x UK, clone 33-1-1 (VP7:5 [IAL28]) | ATCC VR-2613 |
| AU32 x UK, clone 27-1-1 (VP7:9 [AU32]) | ATCC VR-2614 |
| KC-1 x UK, clone 32-1-1 (VP7:10 [KC-1]) | ATCC VR-2615 |

Although the foregoing invention has been described in some detail by way of illustration and example for purposes of clarity of understanding, it will be obvious that certain changes and modifications may be practiced within the scope of the appended claims. The scope of the invention should, therefore, be determined not with reference to the above description, but instead should be determined with reference to the appended claims along with their full scope of equivalents.

All publications and patent documents cited in this application are incorporated by reference in their entirety for all purposes to the same extent as if each individual publication or patent document were so individually denoted.

What is claimed is:

1. An immunogenic composition comprising one or more bovine strain reassortant rotavirus and a physiologically acceptable carrier, wherein the one or more bovine strain reassortant rotavirus is deposited with the American Type Culture Collection and is selected from the group consisting of ATCC VR-2611, ATCC VR-2612, ATCC VR-2613, ATCC VR-2614, ATCC VR-2615, ATCC VR-2616, and ATCC VR-2617.

2. The immunogenic composition of claim 1, which comprises ATCC VR-2611, ATCC VR-2612, ATCC VR-2616, and ATCC VR-2617.

3. The composition of claim 1, wherein the physiologically acceptable carrier is a citrate buffer.

4. The composition of claim 1 which further comprises an adjuvant to enhance the immune response.

5. The composition of claim 1, wherein the composition is in a lyophilized form.

6. The composition of claim 1, wherein each bovine strain reassortant rotavirus is formulated to provide a dosage of less than $10^6$ plaque forming units.

7. A method for stimulating the immune system of an infant of less than six months of age, the method comprising administering to the infant the immunogenic composition of claim 1.

8. The method of claim 7, wherein the composition comprises ATCC VR-2611, ATCC VR-2612, ATCC VR-2616, and ATCC VR-2617.

9. The method of claim 7, wherein the composition is administered to the alimentary tract of the infant.

10. The method of claim 7, wherein the composition is administered as a liquid suspension.

11. The method of claim 7, wherein each bovine strain reassortant rotavirus is administered a dosage of less than $10^6$ plaque forming units.

* * * * *